(12) United States Patent
Burnell et al.

(10) Patent No.: US 9,242,045 B2
(45) Date of Patent: Jan. 26, 2016

(54) AUTO-INJECTOR

(75) Inventors: Rosie Burnell, Cambridge (GB);
Timothy Donald Barrow-Williams, Herts (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 270 days.

(21) Appl. No.: 13/876,168

(22) PCT Filed: Oct. 6, 2011

(86) PCT No.: PCT/EP2011/067501
§ 371 (c)(1),
(2), (4) Date: Mar. 27, 2013

(87) PCT Pub. No.: WO2012/045838
PCT Pub. Date: Apr. 12, 2012

(65) Prior Publication Data
US 2013/0204198 A1 Aug. 8, 2013

(30) Foreign Application Priority Data
Oct. 8, 2010 (EP) .................................... 10187005

(51) Int. Cl.
*A61M 5/20* (2006.01)
*A61M 5/32* (2006.01)
(52) U.S. Cl.
CPC ........... *A61M 5/2033* (2013.01); *A61M 5/3202* (2013.01); *A61M 2005/206* (2013.01); *A61M 2005/2073* (2013.01)
(58) Field of Classification Search
CPC ................... A61M 5/2033; A61M 2005/2073; A61M 2005/206; A61M 5/3202; A61M 5/20; A61M 2005/202; A61M 2005/2026; A61M 2005/2086; A61M 2005/2093
See application file for complete search history.

(56) References Cited

U.S. PATENT DOCUMENTS

| | | | |
|---|---|---|---|
| 5,267,963 A * | 12/1993 | Bachynsky | 604/134 |
| 5,865,804 A | 2/1999 | Bachynsky | |
| 6,149,626 A | 11/2000 | Bachynsky et al. | |
| 2010/0185148 A1 * | 7/2010 | Gillespie et al. | 604/110 |

FOREIGN PATENT DOCUMENTS

| WO | 2009098502 A2 | 8/2009 |
|---|---|---|
| WO | WO 2009/098502 * | 8/2009 |

* cited by examiner

*Primary Examiner* — Theodore Stigell
(74) *Attorney, Agent, or Firm* — Fish & Richardson P.C.

(57) ABSTRACT

The invention relates to an auto-injector for administering a dose of a liquid medicament, comprising
a housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
drive means capable of, upon activation:
 pushing the needle from a covered position inside the housing into an advanced position through the orifice and past the proximal end, and
 operating the syringe to supply the dose of medicament, and
activating means arranged to lock the drive means in a loaded state prior to manual operation and capable of, upon manual operation, releasing the drive means for injection, characterized in that the drive means is at least one spring essentially transversally arranged with respect to a longitudinal axis of the syringe at least when in the loaded state.

12 Claims, 10 Drawing Sheets

AUTO-INJECTOR

CROSS REFERENCE TO RELATED APPLICATIONS

The present application is a U.S. National Phase Application pursuant to 35 U.S.C. §371 of International Application No. PCT/EP2011/067501 filed Oct. 6, 2011, which claims priority to European Patent Application No. 10187005.3 filed Oct. 8, 2010. The entire disclosure contents of these applications are herewith incorporated by reference into the present application.

FIELD OF INVENTION

The invention relates to an auto-injector according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide a novel auto-injector.

The object is achieved by an auto-injector according to claim 1.

Preferred embodiments of the invention are given in the dependent claims.

According to the invention, an auto-injector for administering a dose of a liquid medicament comprises:

- a housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
- drive means capable of, upon activation:
- pushing the needle from a covered position inside the housing into an advanced position through the orifice and past the proximal end, and
- operating the syringe to supply the dose of medicament, and
- activating means arranged to lock the drive means in a loaded state prior to manual operation and capable of, upon manual operation, releasing the drive means for injection.

The drive means is at least one spring essentially transversally arranged with respect to a longitudinal axis of the syringe at least when in the loaded state. This may result in a bottle shape of the auto-injector providing improved ergonomics for users with reduced dexterity.

In the context of this specification the term proximal refers to the direction pointing towards the patient during an injection while the term distal refers to the opposite direction pointing away from the patient.

Preferably the spring is arranged as a tension spring. In other embodiments the spring may be a compression spring.

A linkage may be provided for transmitting movement of the drive means into movement of a plunger. The plunger is connected to the syringe and/or the stopper in order to push them in proximal direction. The linkage allows best use of the spring energy, i.e. spring size, stored energy and overall size of the auto-injector can be optimized.

The linkage may comprise at least one arm with two ends, one of the ends having at least one cam follower engaged in a cam track provided in the housing. Said end is connected to the spring while the other end is hinged to the plunger. When the spring is released and starts to contract the end of the arm connected to the spring is guided along the cam track. Thus, depending on the gradient of the cam track, the other end of the arm pushes or pulls the plunger.

In a preferred embodiment the arm is initially in an over-centre position when the spring is in the loaded state. Load of the spring is thus statically resolved into the distal end of the housing. In this context, an over-centre position refers to a situation, where the plunger and the arm form a slightly acute angle so inadvertent release of the spring would not result in movement of the plunger in proximal direction.

The activating means may be a trigger button having a catch engaged with a catch on the arm prior to manual operation. The engaged catches constrain movement of the arm and hence movement of the cam follower along the cam track.

Thus, an accidental bump or knock does not push the plunger over centre in the proximal direction so inadvertent triggering of the auto-injector is avoided. Upon manual operation, i.e. when the trigger button is depressed, the catches disengage so an injection cycle may be started.

The trigger button may be arranged to push against the distal end of the plunger upon manual operation in a manner to push the arm out of its over-centre position resulting in the load of the spring being forwarded to the plunger.

Preferably the trigger button is laterally arranged near the distal end of the housing.

The cam track may be essentially shaped as a tickmark in a manner to provide a bottom dead centre position for the cam follower. In the bottom dead centre position the stopper has almost bottomed out in the syringe. When the cam follower has passed the bottom dead centre the arm pulls the plunger in distal direction so the syringe and the needle are retracted after the end of the injection. For this purpose the plunger has to be attached to the stopper, e.g. by being snapped in or screwed in.

In a preferred embodiment the linkage comprises two arms, each of them having at least one cam follower arranged in its respective cam track. The two arms may be symmetrically arranged in the distal portion. In one embodiment each arm may be connected to one respective spring. In another embodiment both arms are connected to different ends of the same spring.

Usually the hollow needle is equipped with a protective needle shield for keeping the needle sterile and preventing it from being mechanically damaged. The protective needle shield is attached to the needle when the auto-injector or the syringe is assembled.

In a preferred embodiment of the invention a spring clip may be arranged in the housing near the proximal end, the spring clip having a ring shaped portion adapted to an internal diameter of the housing, two spring legs originating from the ring shaped portion towards the proximal end, the legs being inwardly biased in a manner to rest with their proximal ends on a protective needle sheath attached to the needle or to have their proximal ends contact each other when the protective needle sheath is removed leaving but a small aperture between their proximal ends for allowing the needle to pass through. Thus, even when the protective needle sheath is removed, the user is protected from needle stick injuries.

Preferably, the spring clip is made of spring sheet metal. Spring wire or plastic may also be applied.

The proximal ends of the spring clip's legs may exhibit lock features arranged to engage each other and prevent subsequent disengagement.

The spring clip may also be applied in any other injection device.

The plunger may have at least one pin engaged in a longitudinal notch in the housing for guiding the plunger so the plunger's axial alignment is maintained even with its distal end subjected to lateral force components introduced by the arm or arms.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
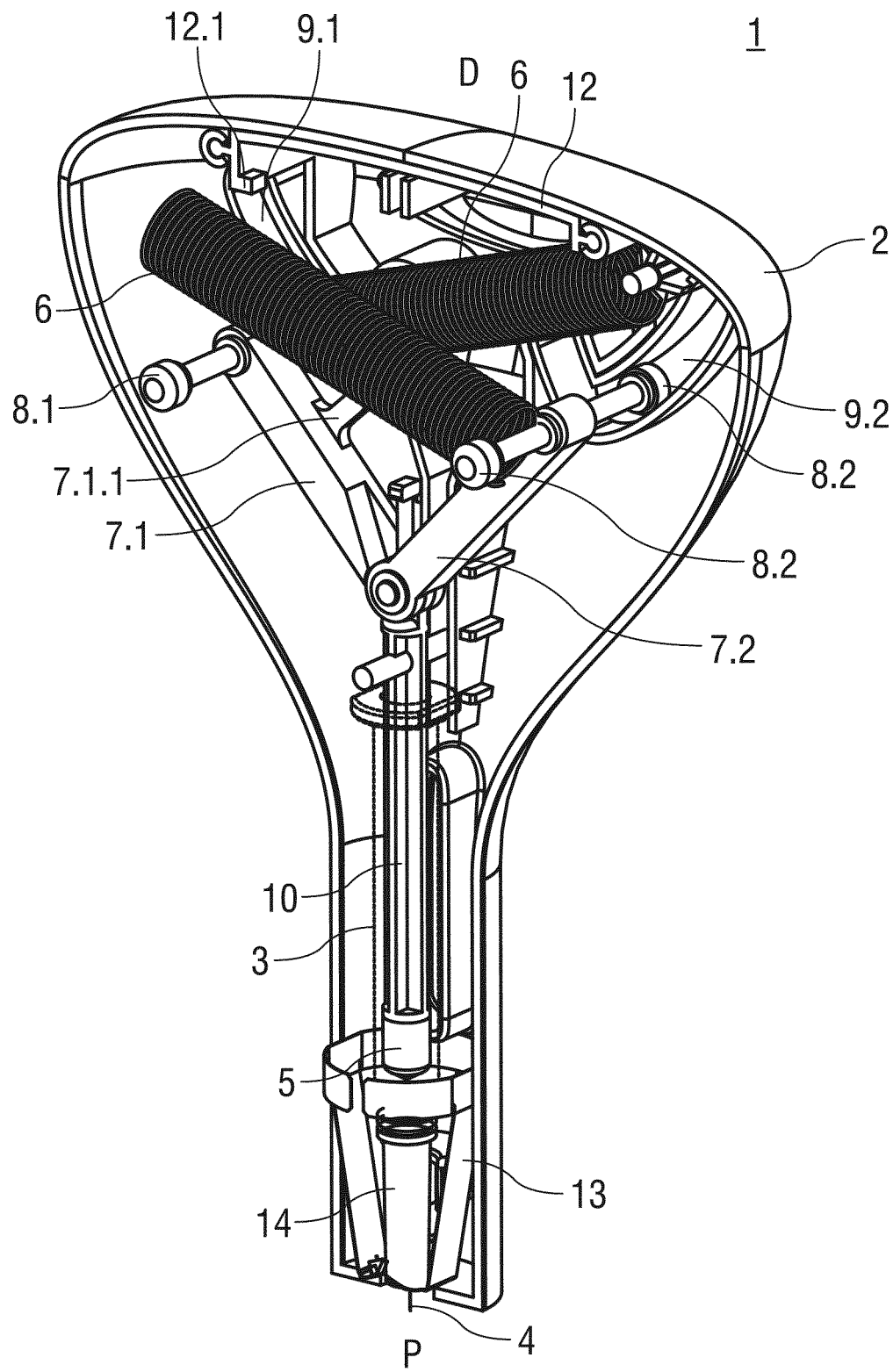
FIG. 1 an isometric view of an auto-injector with two transversal springs.

FIG. 1 shows an isometric view of an auto-injector 1 with a housing 2 arranged to contain a syringe 3 with a hollow injection needle 4 and a stopper 5 for sealing the syringe 3 and displacing a medicament. The housing 2 has a distal end D and a proximal end P with an orifice intended to be applied against an injection site. The syringe 3 is slidably arranged with respect to the housing 2. The auto-injector 1 comprises drive means in the shape of two tension springs 6, which are essentially transversally arranged with respect to a longitudinal axis of the syringe 3 at least when the springs 6 are in a loaded state. The force of the springs 6 is transmitted to the syringe 3 and/or the stopper 5 by means of a linkage 7. The linkage 7 is similar to a scissor jack and comprises two arms 7.1, 7.2. Each arm 7.1, 7.2 has an outer end connected to one of the springs 6 and to a respective cam follower 8.1, 8.2 in the shape of a shaft, each end of the shaft equipped with a roller for engaging in a respective cam track 9.1, 9.2.

Inner ends of the arms 7.1, 7.2 are hinged to each other and to a plunger 10 provided for pushing against the stopper 5.

The cam tracks 9.1, 9.2 are arranged in a manner to allow the springs 6 to push the syringe 3 and the needle 4 from a covered position of the needle inside the housing 2 into an advanced position through the orifice and past the proximal end P. Furthermore, the springs 6 may operate the syringe 3 to supply a dose of medicament M and retract the syringe 3 and needle 4 when the dose has been delivered.

Figure 2:
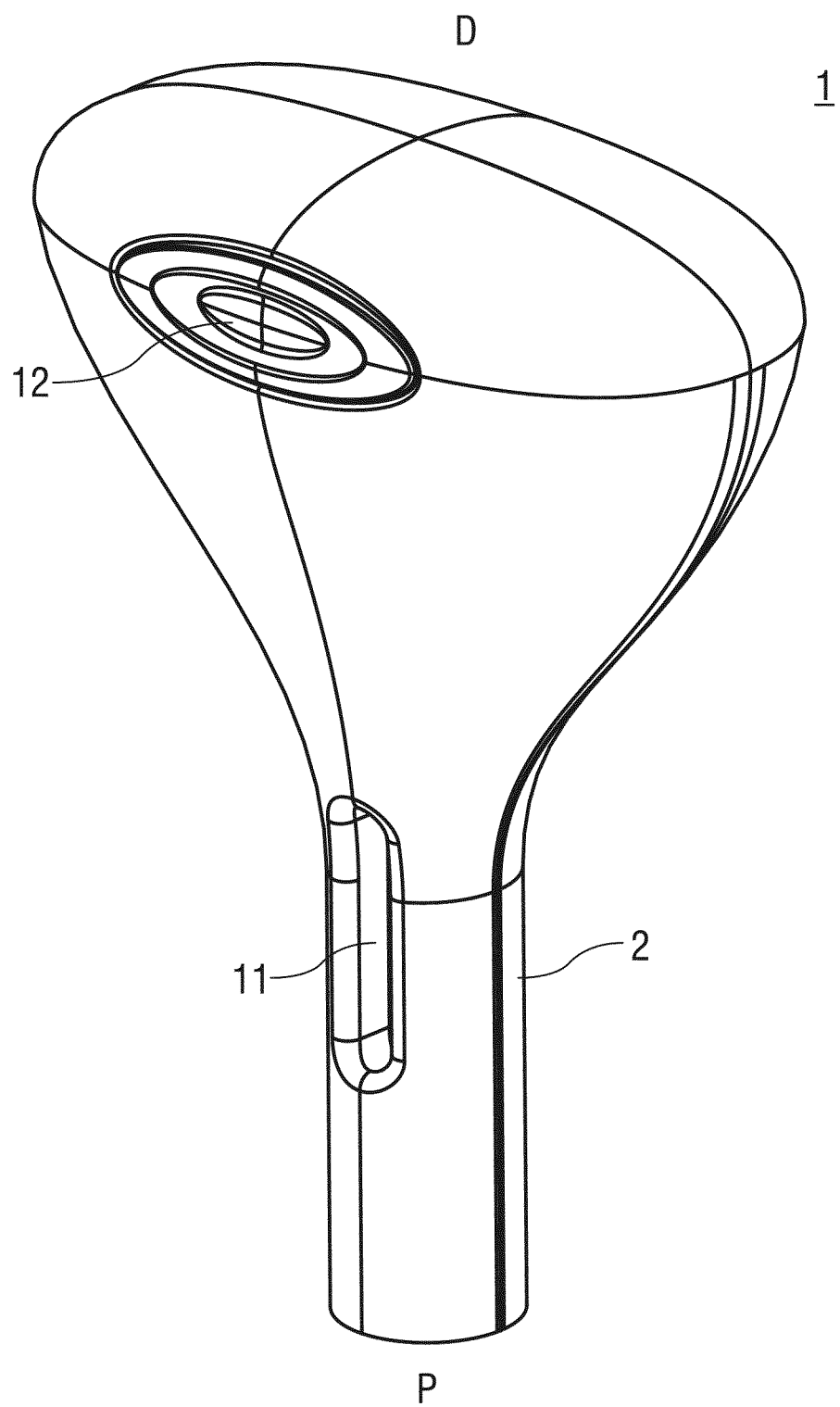
FIG. 2 an isometric view of a housing of the auto-injector.

Due to the orientation of the springs 6 the shape of the housing 2 is similar to a bottle, a proximal portion of the housing 2 being the neck and a distal portion being a flattened body tapering towards the neck (see FIG. 2). A viewing window 11 is provided in the proximal portion for inspecting the syringe contents.

A trigger button 12 for activating an injection is laterally arranged in the distal portion of the housing.

Figure 3:
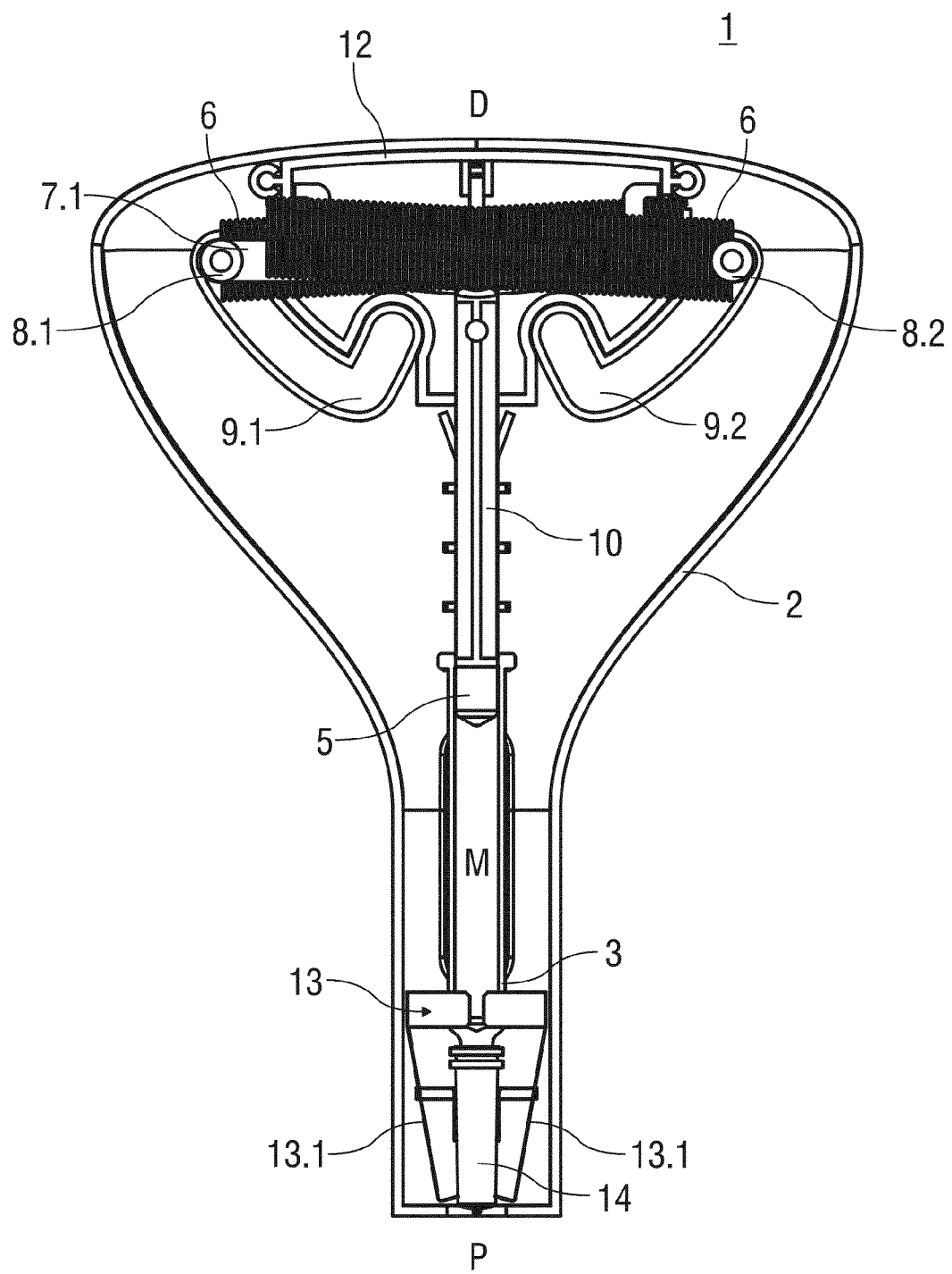
FIG. 3 a longitudinal section of the auto-injector in an initial position with the springs in a loaded state, FIG. 4 a longitudinal section of the auto-injector with a needle shield removed, FIG. 5 a detail view of a proximal part of the auto-injector with a finger guard, FIG. 6 a close-up partial view of the finger guard, FIG. 7 a detail view of a distal part of the auto-injector with a release mechanism, FIG. 8 another detail view of the distal part of the auto-injector with the release mechanism, FIG. 9 a lateral view of the auto-injector with a needle inserted into an injection site, FIG. 10 a lateral view of the auto-injector during injection of a medicament, FIG. 11 a lateral view of the auto-injector with the medicament almost entirely delivered, and FIG. 12 a lateral view of the auto-injector with the syringe and needle retracted from the injection site.
Figure 5:
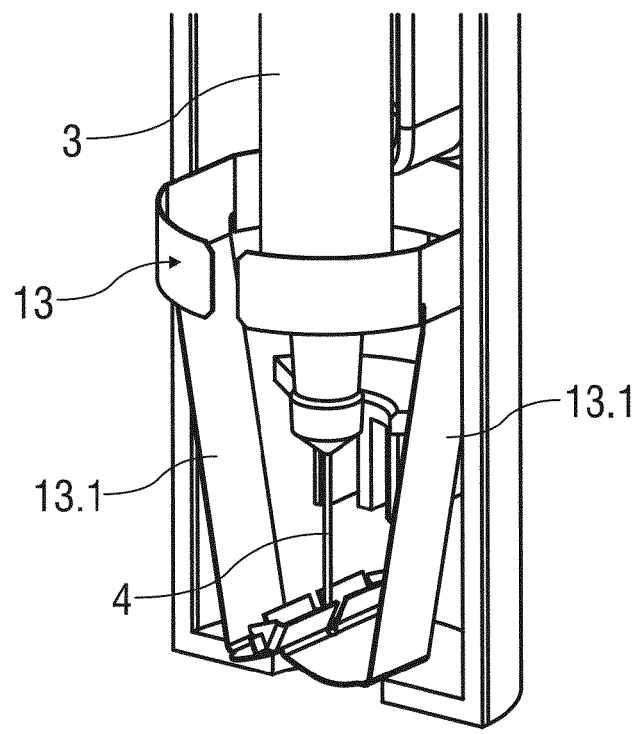
Figure 6:
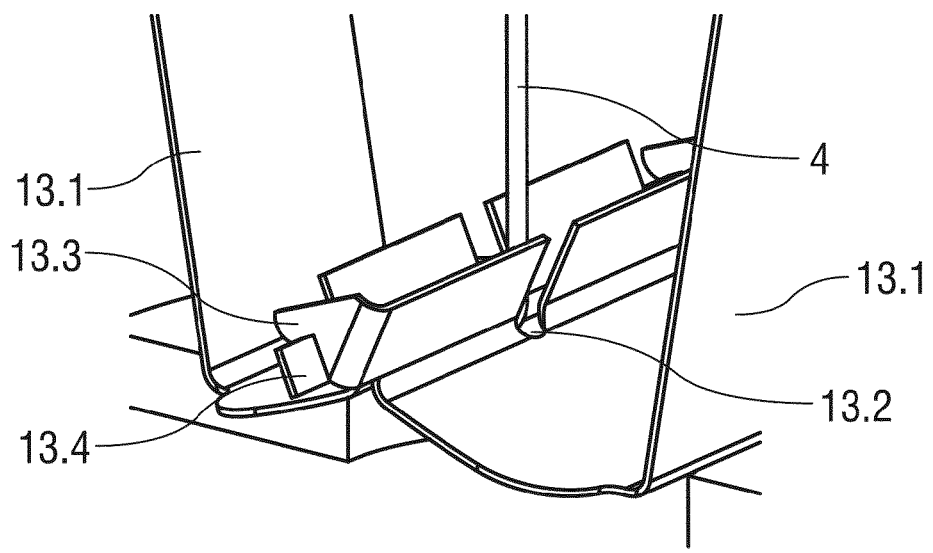

FIG. 3 shows the auto-injector in an initial position as shipped. The springs 6 and the arms 7.1, 7.2 are essentially transversally aligned, wherein the arms are in an over-centre position leaning slightly towards the distal end D. Therefore, the load from the springs 6 acts in distal direction D and is statically resolved in the housing 2. A needle guard in the shape of a spring clip 13 is arranged near the proximal end P for preventing needle stick injuries by keeping users from poking their fingers through the orifice into the housing 2. The needle guard is illustrated in more detail in FIGS. 5 and 6. In the initial state shown in FIG. 3 the needle 4 is covered by a protective needle sheath 14 for keeping the needle 4 sterile and preventing it from being mechanically damaged. The protective needle sheath 14 is attached to the needle 4 when the syringe 3 is assembled. In the initial position the protective needle sheath 14 is held between two inwardly biased spring legs 13.1 of the spring clip 13.

Figure 4:
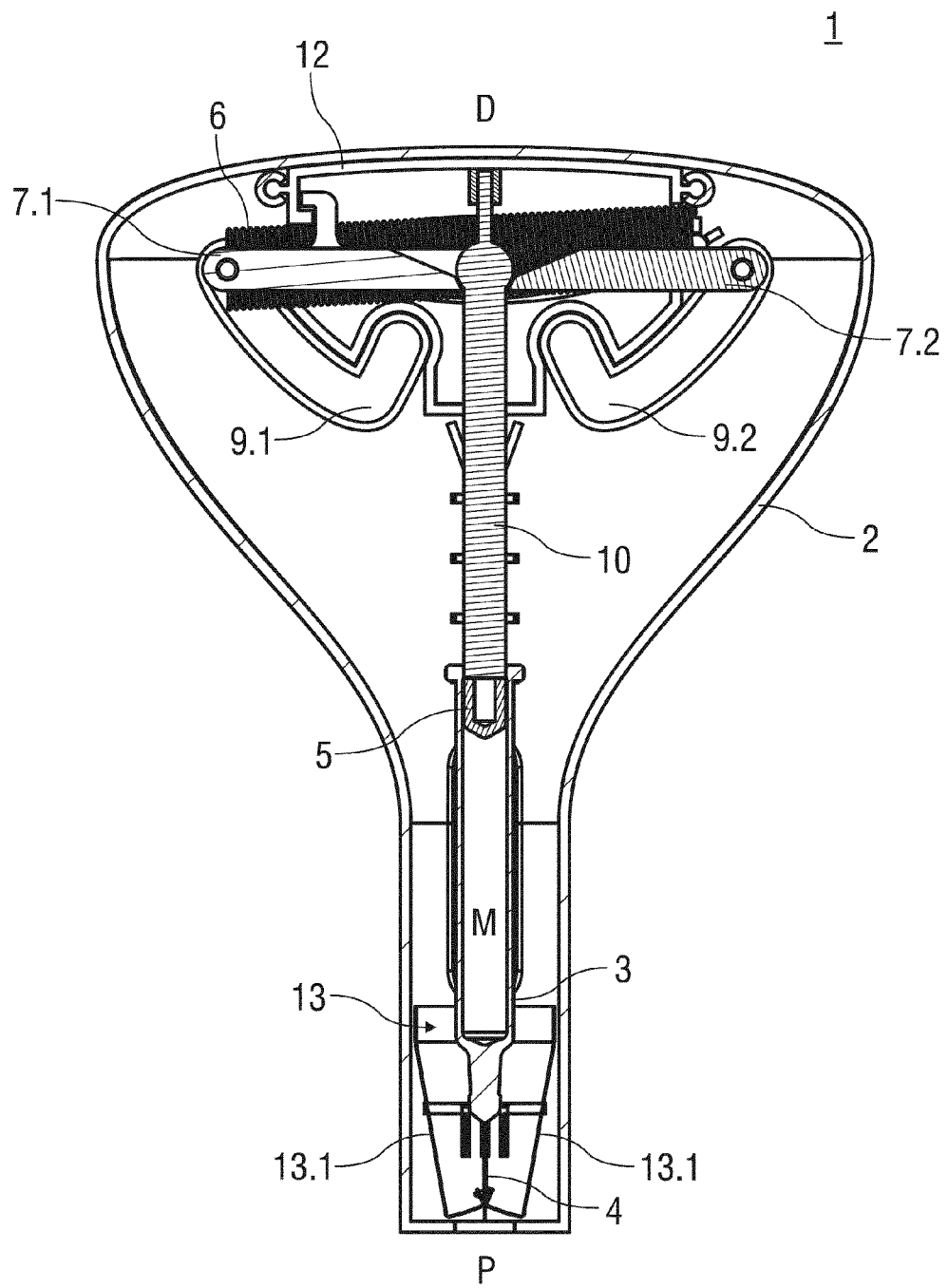

In order to start an injection, the user has to remove the protective needle sheath 14 from the needle 4. Consequently, the inwardly biased spring legs 13.1 move inwards leaving but a small aperture 13.2 for the needle 4 to pass through (see FIGS. 4, 5 and 6). Corresponding lock features 13.3, 13.4 of the spring legs 13.1 engage with each other and prevent the spring legs 13.1 from being again pushed outwards.

Removal of the protective needle sheath 14 may be facilitated by a device cap (not illustrated) designed to grip the protective needle sheath 14.

Figure 7:
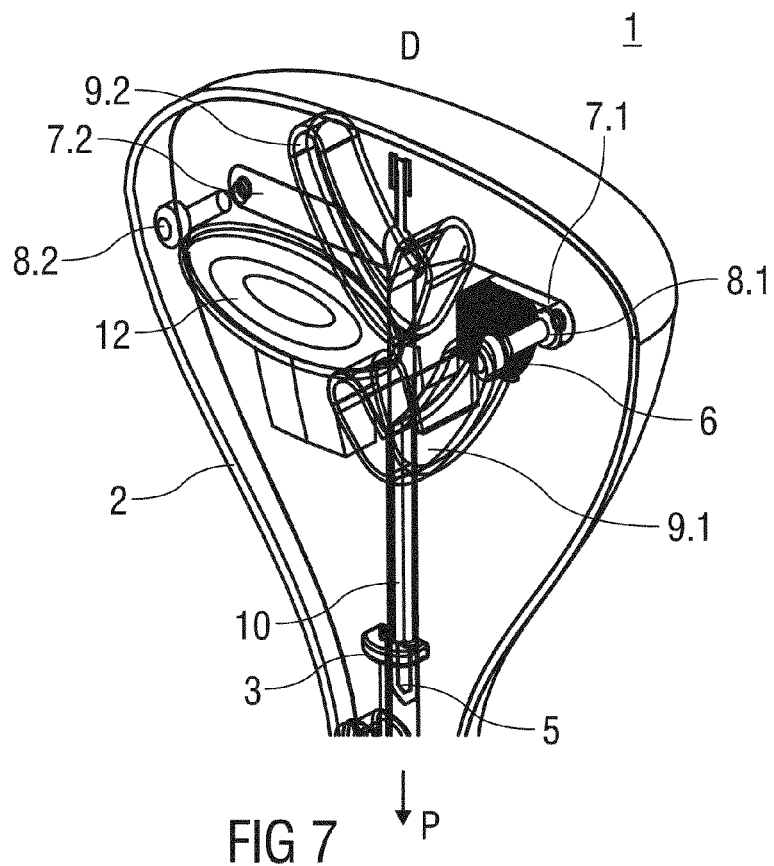
Figure 8:
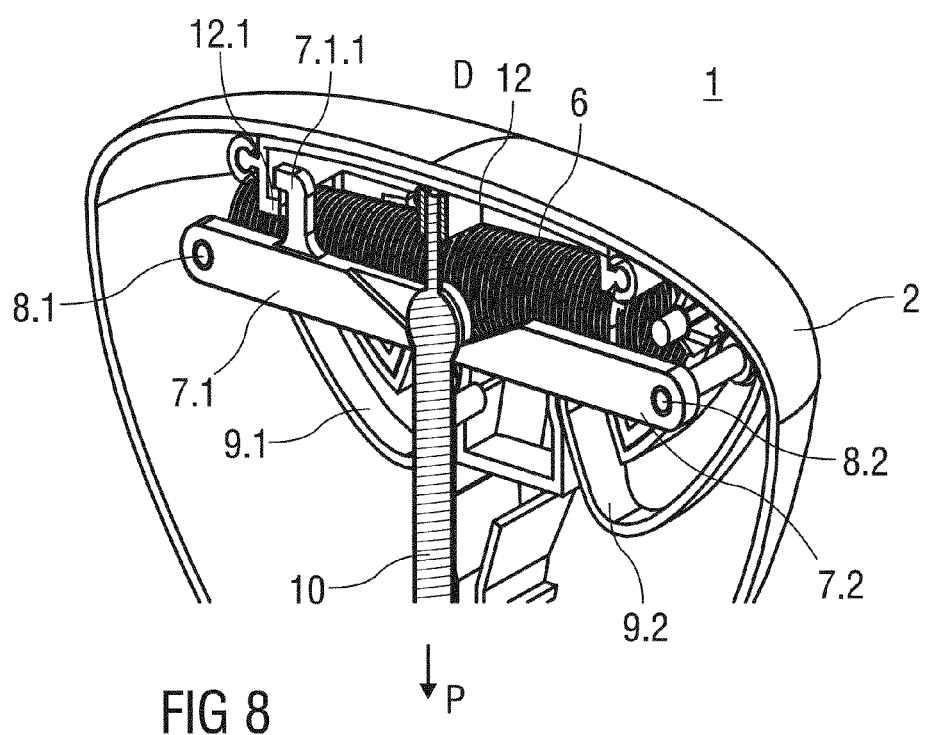

FIGS. 7 and 8 are detail views of the distal portion of the auto-injector 1 with a release mechanism. When the lateral trigger button 12 is not pushed a catch 12.1 on the trigger button 12 is engaged with a catch 7.1.1 in one of the arms 7.1 of the linkage 7 in a manner to constrain movement of the arm 7.1.

The trigger button 12 may be engaged with both arms 7.1, 7.2 in the same manner.

Figure 9:
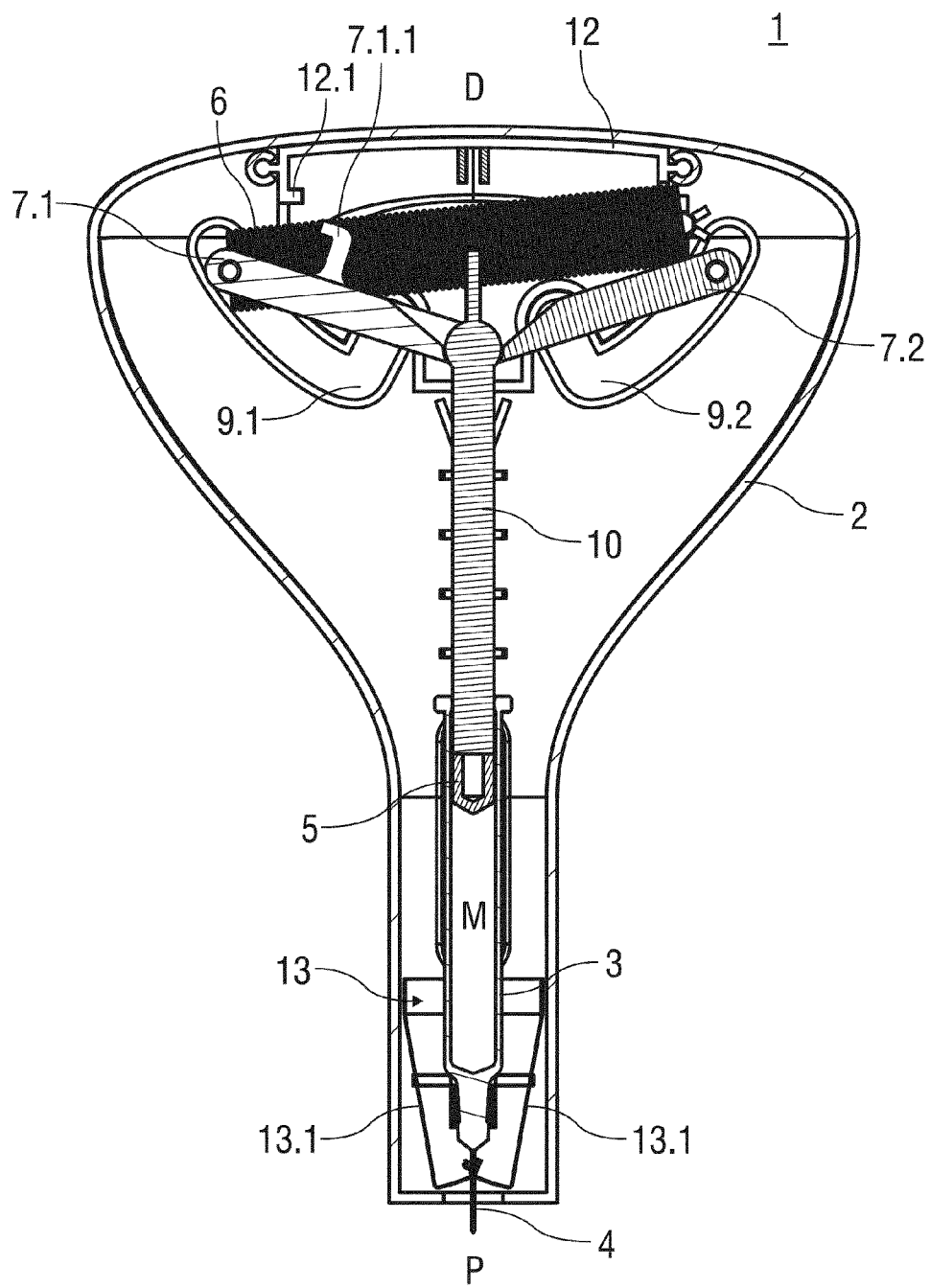

When the trigger button 12 is pushed inwardly the catches 12.1, 7.1.1 are disengaged from each other so movement of the arm 7.1 is no longer constrained. A distal end of the plunger 10 is then pushed in proximal direction P by the button 12, e.g. by an inclined inner surface of the trigger button 12. Thus, by pushing the distal end of the plunger 10 in proximal direction P, the inner ends of the arms 7.1, 7.2 are moved over centre in proximal direction P. Consequently, the load from the springs 6 causes the cam followers 8.1, 8.2 to move along the respective cam track 9.1, 9.2 so the plunger 10 is forced in proximal direction P by the linkage 7. The plunger 10 pushes against the stopper 5. Due to the hydrostatic resistance of the liquid medicament M constrained from being pushed through the narrow fluid channel of the hollow injection needle 4 the syringe 3 is moved in proximal direction P thus inserting the needle 4 into an injection site, e.g. a patient's skin (see FIG. 9). An injection depth is defined by a proximal end of the syringe 3 contacting features inside the proximal portion of the housing 2. Thus, shock forces are transmitted through the strongest part of the syringe 3, thereby minimising the risk of syringe damage or breakage. Due to the shape of the cam tracks 9.1, 9.2 the motion of the mechanism is such that the needle insertion is done quickly, i.e. a small movement of the cam followers 8.1, 8.2 produces a large axial movement of the plunger 10.

Figure 10:
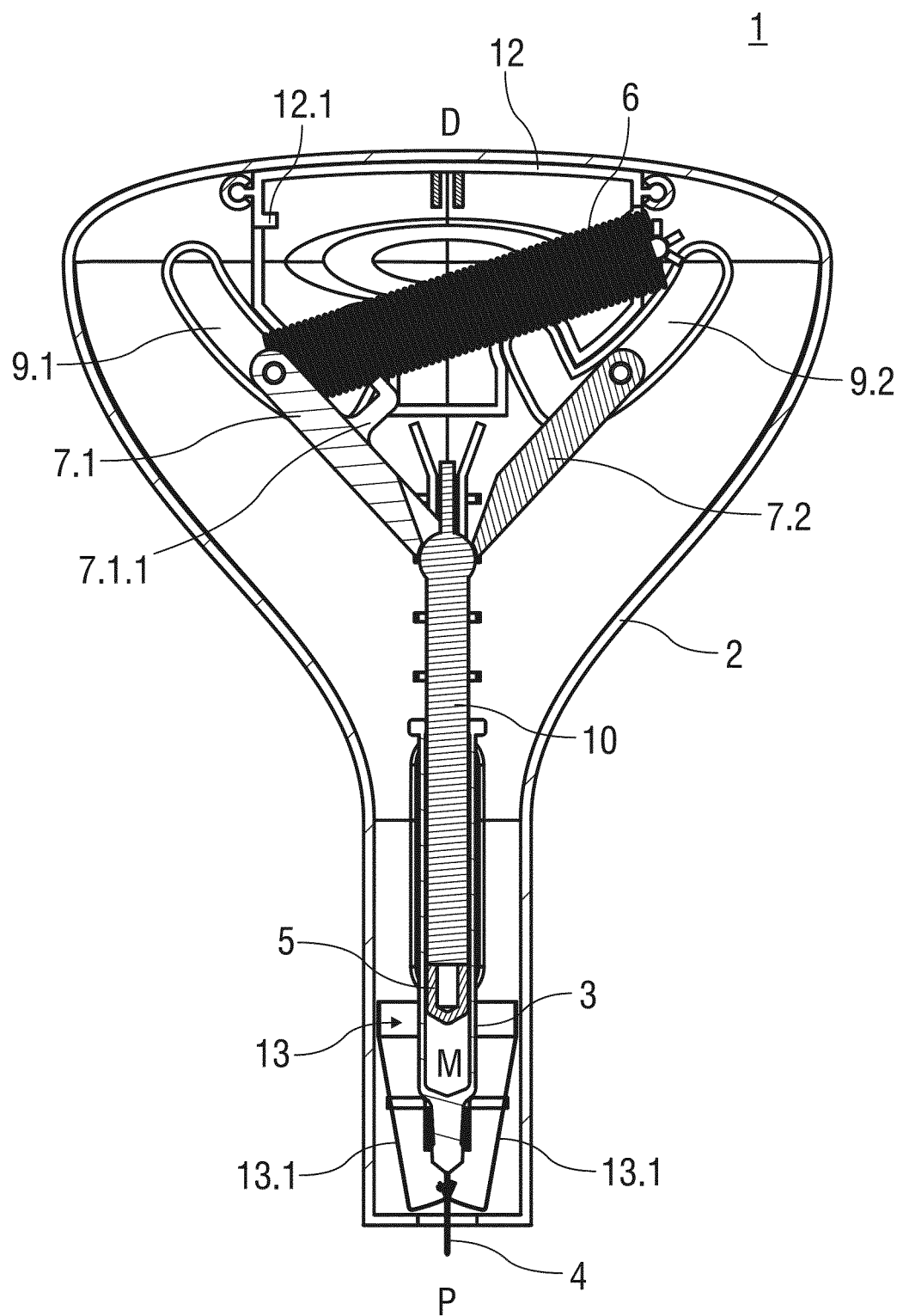

As the cam followers 8.1, 8.2 continue to roll along the cam tracks 9.1, 9.2 the dose of medicament M is expelled from the syringe 3 (see FIG. 10). The profile of the cam tracks 9.1, 9.2 is chosen to compensate the decreasing force of the springs 6 in order to apply a fairly even load to the stopper 5 throughout the injection.

Figure 11:
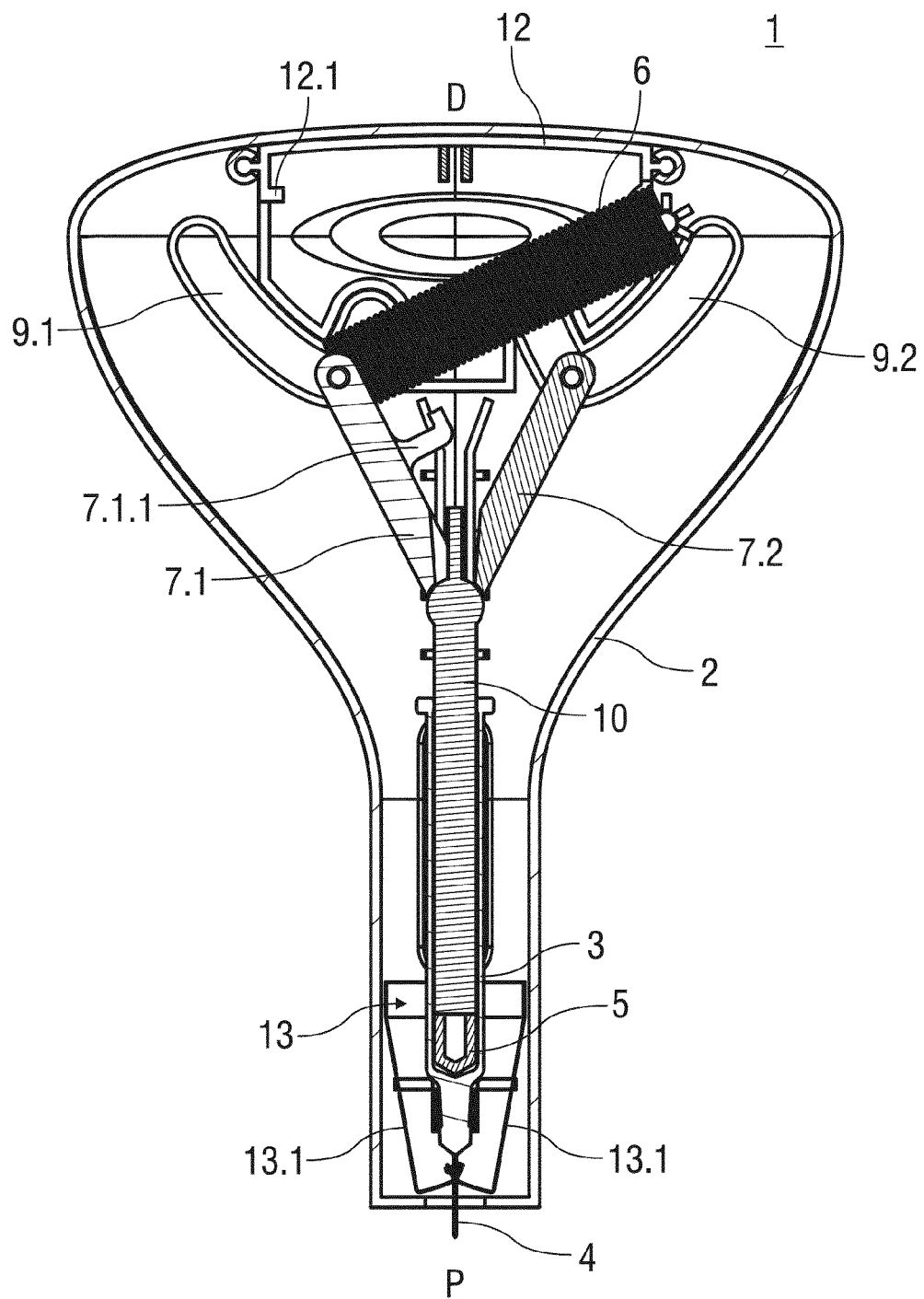

In FIG. 11 the cam followers 8.1, 8.2 have reached a bottom dead centre position in the tickmark shaped cam tracks 9.1, 9.2. This occurs a short distance before the stopper 5 bottoms out in the syringe 3.

Figure 12:
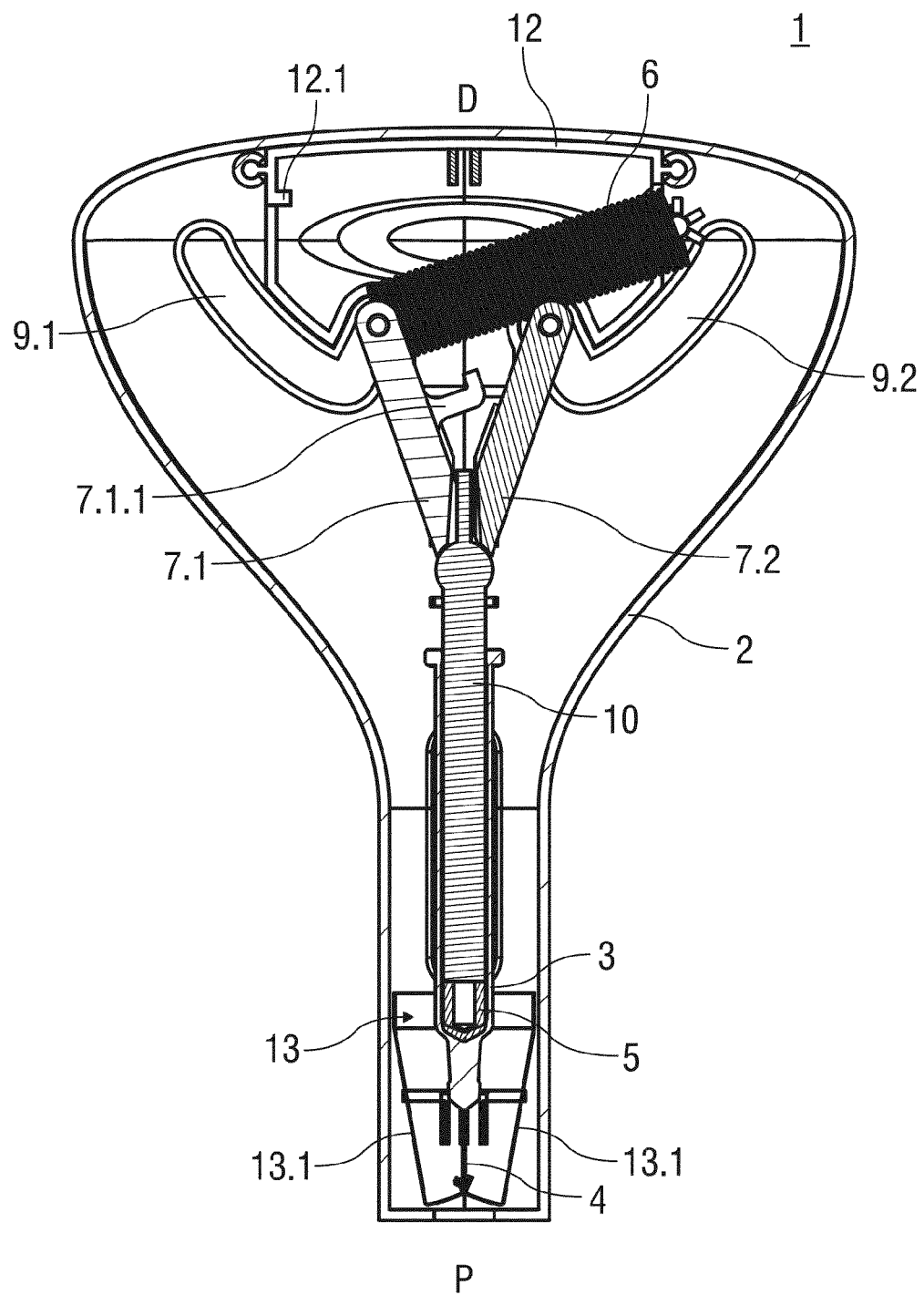

As the cam followers 8.1, 8.2 pass the bottom dead centre position the load on the plunger 10 is reversed in a manner to pull it in distal direction D (see FIG. 12). Since the proximal end of the plunger 10 is attached to the stopper 5, e.g. by being snapped in or screwed in, the stopper 5 is also pulled in distal direction D, so it does not entirely bottom out in the syringe 3 in order to avoid stalling before the retraction starts. Friction between the stopper 5 and an inner wall of the syringe 3 is greater than a force required to remove the needle 4 from the injection site. Hence, by pulling the stopper 5 in distal direction D the needle 4 and syringe 3 are being retracted resulting in the needle being hidden inside the housing 2.

Alternative embodiments could by implemented with only one transversal spring 6 and/or with compression springs instead of tension springs. A decoupling mechanism could be applied for forwarding the force from the plunger 10 to the syringe 3 without pushing on the stopper 5 until the injection depth is reached in order to avoid wet injection. After reaching the injection depth the plunger 10 could be decoupled from the syringe 3 and coupled to the stopper 5 in order to expel the medicament M from the syringe 3. Yet improved embodiments could comprise damping or delay mechanisms for allowing to completely empty the syringe when the cam followers have passed the bottom dead centre position.

The invention claimed is:

1. Auto-injector for administering a dose of a liquid medicament, comprising
   a housing arranged to contain a syringe with a hollow needle and a stopper for sealing the syringe and displacing the medicament, the housing having a distal end and a proximal end with an orifice intended to be applied against an injection site, wherein the syringe is slidably arranged with respect to the housing,
   a plunger connected to at least one of the syringe and the stopper,
   a drive mechanism comprising at least one spring essentially transversally arranged with respect to a longitudinal axis of the syringe at least when the drive mechanism is in a loaded state capable of, upon activation:
      pushing the needle from a covered position inside the housing into an advanced position through the orifice and past the proximal end, and
      operating the syringe to supply the dose of medicament,
   an activating mechanism arranged to lock the drive mechanism in the loaded state prior to manual operation and capable of, upon manual operation, releasing the drive mechanism for injection, and
   a linkage and cam mechanism configured to transmit movement of the drive mechanism into movement of the plunger, a linkage of the linkage and cam mechanism comprising at least one arm with a first end and a second end, the first end having at least one cam follower engaged in a cam track provided in the housing and being hinged to the at least one spring, the second end being hinged to the plunger.

2. Auto-injector according to claim 1, characterized in that the spring is arranged as a tension spring.

3. Auto-injector according to claim 1, characterized in that in the loaded state the arm is in an over-centre position statically resolving load of the spring into the distal end of the housing.

4. Auto-injector according to claim 1, characterized in that the activating mechanism comprises a trigger button having a catch engaged with a catch of the arm prior to manual operation, the engaged catches arranged to constrain movement of the cam follower along the cam track, wherein the trigger button is arranged to disengage the catches upon manual operation.

5. Auto-injector according to claim 3, characterized in that the activating mechanism comprises a trigger button arranged to push against the distal end of the plunger upon manual operation in a manner to push the arm out of its over-centre position resulting in the load of the spring being forwarded to the plunger.

6. Auto-injector according to claim 4, characterized in that the trigger button is laterally arranged near the distal end.

7. Auto-injector according to claim 1, characterized in that the cam track is essentially shaped as a tickmark in a manner to provide a bottom dead centre position for the cam follower, in which the stopper has almost bottomed out in the syringe and in a manner to allow the arm, plunger, syringe and needle to be retracted after the cam follower has passed the bottom dead centre.

8. Auto-injector according to claim 1, characterized in that two arms are provided, each of them having at least one cam follower arranged in its respective cam track.

9. Auto-injector according to claim 8, characterized in that each arm is connected to one respective spring.

10. Auto-injector according to claim 1, characterized in that a spring clip is arranged in the housing near the proximal end, the spring clip having a ring shaped portion adapted to an internal diameter of the housing, two spring legs originating from the ring shaped portion towards the proximal end, the legs being inwardly biased in a manner to rest with their proximal ends on a protective needle sheath attached to the needle or to have their proximal ends contact each other when the protective needle sheath is removed leaving but a small aperture between their proximal ends for allowing the needle to pass through.

11. Auto-injector according to claim 10, characterized in that the proximal ends of the legs exhibit lock features arranged to engage each other and prevent subsequent disengagement.

12. Auto-injector according to claim 1, characterized in that the plunger has at least one pin engaged in a longitudinal notch in the housing for guiding the plunger.

* * * * *